United States Patent
Rama et al.

(10) Patent No.: US 12,036,034 B2
(45) Date of Patent: Jul. 16, 2024

(54) KNEE LIGAMENT EVALUATION SYSTEM AND METHOD

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Suraj Rama, Pittsburgh, PA (US); Samuel C. Dumpe, Beaver, PA (US); Ryan Sheehan, Pittsburgh, PA (US); Benjamin McCandless, Pittsburgh, PA (US)

(73) Assignees: Smith & Nephew, Inc.; Smith & Nephew Orthopaedics AG, Zug (CH); Smith & Nephew Asia Pacific Pte. Limited, Singapore (SG)

(*) Notice: Subject to any disclaimer, the term of this patent is extended or adjusted under 35 U.S.C. 154(b) by 0 days.

(21) Appl. No.: 18/216,003

(22) Filed: Jun. 29, 2023

(65) Prior Publication Data

US 2023/0337968 A1    Oct. 26, 2023

Related U.S. Application Data

(63) Continuation of application No. 17/335,919, filed on Jun. 1, 2021, now Pat. No. 11,723,587.

(Continued)

(51) Int. Cl.
*A61B 17/02* (2006.01)
*A61B 5/00* (2006.01)
(Continued)

(52) U.S. Cl.
CPC .......... *A61B 5/4533* (2013.01); *A61B 5/4585* (2013.01); *A61B 17/1764* (2013.01);
(Continued)

(58) Field of Classification Search
CPC ...................... A61B 2017/0268; A61B 5/4585
See application file for complete search history.

(56) References Cited

U.S. PATENT DOCUMENTS

| 8,211,041 B2 | 7/2012 | Fisher et al. |
| 9,351,850 B2 | 5/2016 | Fischer et al. |

(Continued)

FOREIGN PATENT DOCUMENTS

| WO | 2020033579 A1 | 2/2020 |
| WO | 2020033589 A1 | 2/2020 |

(Continued)

*Primary Examiner* — Samuel S Hanna
(74) *Attorney, Agent, or Firm* — KDW Firm PLLC

(57) ABSTRACT

Disclosed herein is a joint evaluation device and corresponding systems and methods for evaluating ligaments and other soft tissue connections between, for example, a tibia and a femur at a knee joint. The joint evaluation device being arranged and configured to induce and measure forces while positions of the tibia and femur are monitored. Some embodiments use a computer assisted surgery device to track positions of the tibia and the femur, and may include a computing device configured to evaluate the forces measured between a first engagement portion and a second engagement portion of the joint evaluation device to output information related to the status of the ligament and other soft tissue connections prior to any bone resections being made to the tibia or the femur.

14 Claims, 7 Drawing Sheets

Related U.S. Application Data

(60) Provisional application No. 63/034,579, filed on Jun. 4, 2020.

(51) Int. Cl.
  *A61B 17/17* (2006.01)
  *A61B 34/10* (2016.01)

(52) U.S. Cl.
  CPC ...... *A61B 34/10* (2016.02); *A61B 2562/0247* (2013.01); *A61B 2562/046* (2013.01)

(56) References Cited

U.S. PATENT DOCUMENTS

| | | |
|---|---|---|
| 9,649,119 B2 | 5/2017 | Rock et al. |
| 9,993,354 B2 | 6/2018 | Fisher et al. |
| 10,070,972 B2 | 9/2018 | Maher et al. |
| 10,098,761 B2 | 10/2018 | Sherman et al. |
| 10,172,723 B2 | 1/2019 | Fisher et al. |
| 2015/0342588 A1 | 12/2015 | Bechtold et al. |
| 2019/0388078 A1 | 12/2019 | Otto et al. |
| 2020/0155135 A1* | 5/2020 | Cole ................. A61B 17/8869 |
| 2021/0085305 A1 | 3/2021 | Corpa De La Fuente et al. |
| 2021/0106320 A1 | 4/2021 | Bechtold et al. |
| 2023/0072295 A1 | 3/2023 | McCandless et al. |

FOREIGN PATENT DOCUMENTS

| | | |
|---|---|---|
| WO | 2020047051 A1 | 3/2020 |
| WO | 2020176128 A1 | 9/2020 |
| WO | 2021141830 A1 | 7/2021 |
| WO | 2021163276 A1 | 8/2021 |

* cited by examiner

KNEE LIGAMENT EVALUATION SYSTEM AND METHOD

CROSS-REFERENCE TO RELATED APPLICATIONS

This application is a continuation application of U.S. patent application Ser. No. 17/335,919, filed Jun. 1, 2021, which application is a non-provisional of, and claims the benefit of the filing date of, U.S. provisional patent application No. 63/034,579, filed Jun. 4, 2020, entitled "Knee Ligament Evaluation System and Method," the entirety of each application is incorporated by reference herein.

TECHNICAL FIELD

The present disclosure relates generally to the field of medical instruments, and more particularly relates to a system and method that uses a surgical instrument or device to separate first and second bones at a joint such as, for example, a tibia and a femur at a knee joint, to evaluate ligament and other soft tissue connections between the first and second bones at the joint (e.g., the tibia and the femur at the knee joint). More particularly, in one embodiment, the surgical instrument or device separates the tibia and the femur under a measured separation force and evaluates the separation caused by the force using a computer assisted surgery (CAS) system or devices.

BACKGROUND

Orthopedic implants are well known and commonplace in today's society. For example, a knee replacement or arthroplasty is a well-known surgical procedure. When performing a typical knee arthroplasty, a quantitative assessment of soft tissue forces (e.g., laxity) before or prior to bony resection would be useful in estimating, for example, resection location, implant sizes to use for the arthroplasty, evaluating underlying pathologies, and setting goals for post-implantation soft tissue tensions that are desirable.

Surgeons, however, have limited tools to quantitatively assess soft tissue laxity prior to making resections of the patient's bone. As a result, surgeons typically resort to inserting a metal instrument or device into the joint gap. For example, a surgeon may insert an instrument such as, for example, a PCL retractor, into a patient's knee joint. However, inserting a PCL retractor into the patient's knee joint results in the creation of a gap in the patient's joint and thus reduces the minimum joint gap that can be measured (e.g., insertion of the PCL retractor into the joint gap reduces a surgeon's ability to measure a minimum gap or distance between the patient's tibia and femur since the PCL retractor introduces a gap or distance corresponding to the thickness or height of the PCL retractor).

That is, currently, after a bony resection in a typical procedure, tools such as spacers and trials are used to assess resulting soft tissue tension or laxity. If a joint is found to be in an unbalanced state after implantation, the likely response is to release one or more ligaments (e.g., surgeon may utilize an osteotome to perform incisions along the ligaments connection to the bone). The less accurate a prosthetic joint sizing is found to be, the more drastic ligament releases may have to be. When performing CAS arthroplasty, such as robotically assisted total knee arthroplasty, soft tissue pre- and post-resection evaluations may be accomplished by a user applying *varus* and valgus movements to the knee joint through a range of motion. These movements are typically applied manually, or with a z-retractor between the medial and the lateral tibiofemoral articular surfaces. A computer-based tracking system and related computer and software, such as a CAS system, are capable of assessing soft tissue laxity. However, such systems fail to precisely quantify the forces being applied to create the *varus* and valgus movements tracked and recorded. Therefore, there is a significant challenge associated with accurately and consistently quantifying soft tissue laxity where a CAS system is being used to track and record *varus* and valgus movements.

As such, overall patient satisfaction with knee joint arthroplasty generally lags behind other surgical procedures. For example, a common patient complaint is that the knee implant doesn't feel right (e.g., doesn't feel like the native joint prior to implant insertion). Thus, a surgical instrument or device and corresponding methods for measuring a joint gap laxity prior to joint distraction or bony resection would be beneficial to assist surgeons with producing a "balanced knee". Generally speaking, a balanced knee is a post-operative knee with equal tension in ligaments and distance between bones (e.g., tibial and femur) such as, for example, equal sized flexion and extension gaps, rectangular gaps in flexion and extension and medial and lateral planes, and/or equal sized gaps or distances between the patient's tibial and the patient's medial and lateral condyles. As such, a system capable of quantifying forces applied to a joint that result in specific movements of the joint would be beneficial. An improved system may further be capable of associating soft tissue conditions and pathologies with the applied forces.

It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is a joint evaluation device for assessing soft tissues of a joint such as, for example, a knee joint. In one embodiment, the joint evaluation device includes a body, a first engagement portion coupled to the body, and a second engagement portion coupled to the body. The joint evaluation device may also include an actuator coupled to the body and configured to move the first and second engagement portions relative to each other, and a force measurement device arranged and configured to evaluate a force applied between the first and second engagement portions (e.g., a force required to move one or both of the engagement portions through the joint space).

In addition, a system for evaluating ligament and other soft tissue connections between bones such as, for example, a tibia and a femur at a knee joint is disclosed. In one embodiment, the system includes a joint evaluation device, a computer assisted surgery (CAS) system or device, and a computing device. The joint evaluation device may include a body, a first engagement portion coupled to the body, a second engagement portion coupled to the body, an actuator coupled to the body and configured to move the first and second engagement portions relative to each other, and a force measurement device arranged and configured to evaluate a force applied between the first and second engagement portions. The CAS system or device may be arranged and configured to track relative locations of the tibia and the femur, and the computing device may be arranged and configured to evaluate the forces measured between the first and second engagement portions to output information related to the status of the ligament and other soft tissue connections between the tibia and the femur prior to any bone resections being made to the tibia or the femur.

A method of evaluating the soft tissues of a knee is also disclosed. In one embodiment, the method includes inserting a first engagement portion and a second engagement portion of a joint evaluation device into a knee joint of a patient between a femur and a tibia, moving the first engagement portion and the second engagement portion of the joint evaluation device relative to each other to create a relative movement of the femur and the tibia, and measuring the force required to move the first engagement portion and the second engagement portion of the joint evaluation device relative to each other to create a relative movement of the femur and the tibia. In one embodiment, the method may also include measuring the relative movement of the femur and the tibia, calculating information related to the status of the ligament and other soft tissue connections between the tibia and the femur based on the force required to move the first engagement portion and the second engagement portion of the joint evaluation device relative to each other and the measured relative movement of the femur and the tibia prior to any bone resections being made to the tibia or the femur, and using the calculated information to output surgical instructions.

In one embodiment, a joint evaluation device arranged and configured to assess soft tissues of a knee joint is disclosed. The joint evaluation device includes a body, a first engagement portion coupled to the body, a second engagement portion coupled to the body, an actuator, and a force measurement device. The actuator being coupled to the body and configured to move the first and second engagement portions relative to each other such that, in use, the second engagement portion moves laterally towards the first engagement portion through the knee joint to create a relative movement between a patient's tibia and femur. The force measurement device being arranged and configured to evaluate a force applied between the first and second engagement portions required to move the second engagement portion laterally towards the first engagement through the knee joint.

In one embodiment, the body includes a handle configured to be grasped by a user.

In one embodiment, the first engagement portion includes a first face arranged and configured at an oblique angle to a direction of motion between the first and second engagement portions.

In one embodiment, the joint evaluation device further includes a first array of force sensors on the first face. In one embodiment, the first array of force sensors is an array of pressure sensors. In one embodiment, the second engagement portion includes a second face arranged and configured at an oblique angle to the direction of motion between the first and second engagement portions. In one embodiment, the joint evaluation device further includes a second array of force sensors on the second face. In one embodiment, the second array of force sensors is an array of pressure sensors.

In one embodiment, the actuator includes a motor. In one embodiment, the motor is arranged and configured to turn a threaded shaft coupled to the body, the threaded shaft operatively coupled with one or more gears on the second engagement portion to move the second engagement portion relative to the first engagement portion when the motor is activated. In one embodiment, the force measurement device is associated with the motor to measure a force required to turn the motor. In one embodiment, the force measurement device is a torque measuring device.

In one embodiment, the actuator includes a thumbwheel. In one embodiment, the thumbwheel is arranged and configured to turn a threaded shaft, the threaded shaft operatively coupled with one or more gears on the second engagement portion to move the second engagement portion relative to the first engagement portion when the thumbwheel is actuated. In one embodiment, the force measurement device is positioned between the thumbwheel and the body to measure force required to turn the thumbwheel.

In one embodiment, a system for evaluating ligament and other soft tissue connections between a tibia and a femur at a knee joint is disclosed. In one embodiment, the system includes a joint evaluation device, a computer assisted surgery (CAS) device, and a computing device. The joint evaluation device includes a body, a first engagement portion coupled to the body, a second engagement portion coupled to the body, an actuator, and a force measurement device. The actuator being coupled to the body and configured to move the first and second engagement portions relative to each other such that, in use, the second engagement portion moves laterally towards the first engagement portion through the knee joint to create a relative movement between a patient's tibia and femur. The force measurement device being arranged and configured to evaluate a force applied between the first and second engagement portions to move the second engagement portion laterally towards the first engagement through the knee joint. The CAS device being arranged and configured to track a relative location of the tibia and the femur. The computing device being arranged and configured to evaluate the forces measured between the first engagement portion and the second engagement portion to output information related to a status of the ligament and other soft tissue connections between the tibia and the femur prior to any bone resections being made to the tibia or the femur.

In one embodiment, the first engagement portion includes a first face arranged and configured at an oblique angle to a direction of motion between the first and second engagement portions, the first face including an array of force or pressure sensors positioned thereon and the second engagement portion includes a second face arranged and configured at an oblique angle to the direction of motion between the first and second engagement portions, the second face including an array of force or pressure sensors positioned thereon.

In one embodiment, the actuator includes a motor arranged and configured to turn a threaded shaft coupled to the body, the threaded shaft operatively coupled with one or more gears on the second engagement portion to move the second engagement portion relative to the first engagement portion when the motor is activated.

In one embodiment, the force measurement device is associated with the motor to measure force required to turn the motor.

In one embodiment, the actuator includes a manually-activated thumbwheel arranged and configured to turn a threaded shaft coupled to the body, the threaded shaft operatively coupled with one or more gears on the second engagement portion to move the second engagement portion relative to the first engagement portion when the thumbwheel is actuated.

In one embodiment, the force measurement device is positioned between the thumbwheel and the body to measure force required to turn the thumbwheel.

In one embodiment, the output information related to the status of the ligament and other soft tissue connections between the tibia and the femur prior to any bone resections being made to the tibia or the femur includes implant size and location recommendations.

In one embodiment, the output information related to the status of the ligament and other soft tissue connections between the tibia and the femur prior to any bone resections being made to the tibia or the femur includes resection cut position recommendations.

In one embodiment, a method of evaluating a ligament and other soft tissues connections between a patient's tibia and a patient's femur of a knee joint is disclosed. The method including inserting a first engagement portion of a joint evaluation device into a femoral notch of the knee joint between the patient's tibia and femur; positioning a second engagement portion of the joint evaluation device on one of a medial side or a lateral side of the knee joint; moving the first and second engagement portions relative to each other such that the second engagement portion moves laterally towards the first engagement portion to create a relative movement of the patient's tibia and femur; measuring a force required to move the first and second engagement portions relative to each other such that the second engagement portion moves laterally towards the first engagement; measuring the relative movement of the patient's tibia and femur; calculating information related to the status of the ligament and other soft tissues connections between the patient's tibia and femur based on the force required to move the second engagement portion relative to the first engagement portion and the measured relative movement of the patient's tibia and femur prior to any bone resections being made to the patient's tibia and femur; and using the calculated information to output surgical instructions.

In one embodiment, moving the first and second engagement portions relative to each other such that the second engagement portion moves laterally towards the first engagement portion to create a relative movement of the patient's tibia and femur includes wedging apart the patient's tibia and femur with one or both of the first and second engagement portions.

In one embodiment, measuring a force required to move the first and second engagement portions relative to each other such that the second engagement portion moves laterally towards the first engagement includes measuring force on an array of force sensors positioned on one or both of the first engagement portion and the second engagement portion.

In one embodiment, measuring a force required to move the first and second engagement portions relative to each other such that the second engagement portion moves laterally towards the first engagement includes measuring a force required to turn a motor positioned between the first engagement portion and the second engagement portion.

In one embodiment, the output surgical instructions include instructions specifying one of implant size and location recommendations, resection cut position recommendations, or a combination thereof.

Embodiments of the present disclosure provide numerous advantages. In one non-limiting example advantage, the joint evaluation device enables a surgeon to measure joint laxity prior to bony resection.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1:
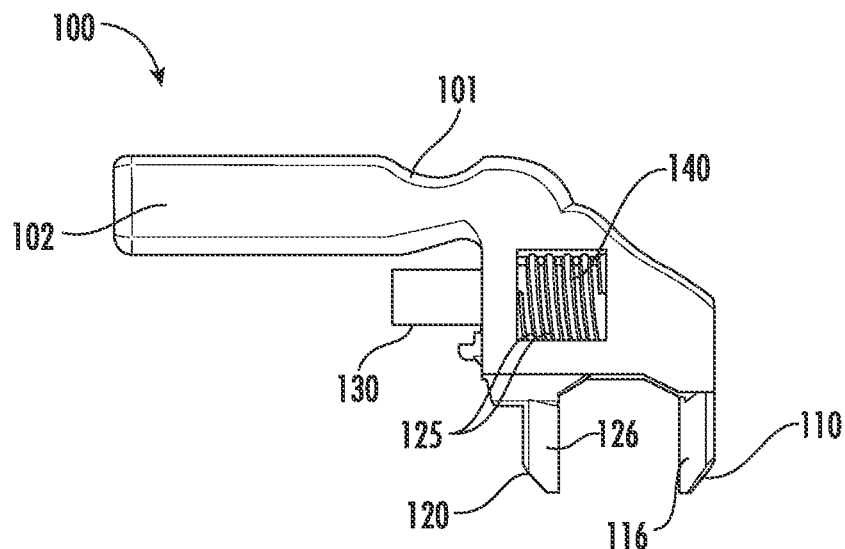
FIG. 1 illustrates a plan view of an embodiment of a joint evaluation device for assessing soft tissues of a joint (e.g., a knee joint) in accordance with one or more features of the present disclosure, the joint evaluation device illustrated in an open state.
Figure 2:
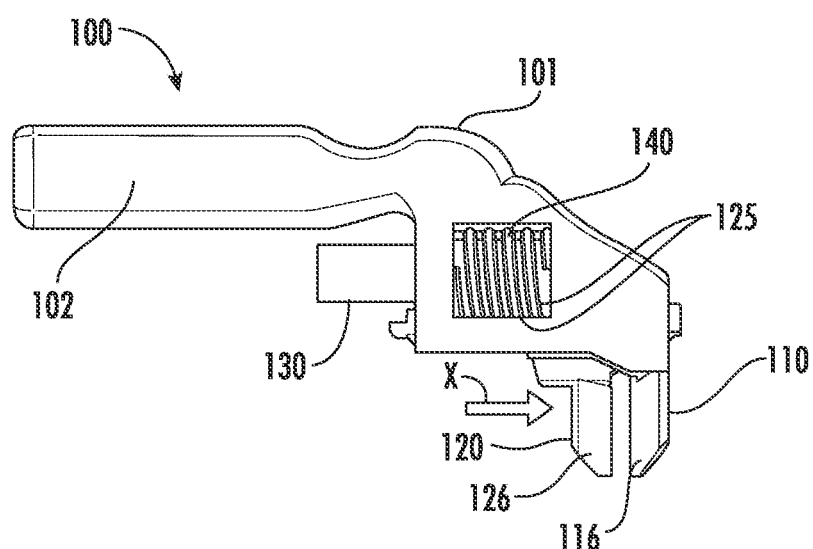
FIG. 2 is a plan view of the joint evaluation device of FIG. 1, the joint evaluation device illustrated in a relatively more closed state.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein. In the drawings, like numbers refer to like elements throughout unless otherwise noted.

DETAILED DESCRIPTION

Various features or the like of a joint evaluation device arranged and configured to measure a joint laxity of a joint prior to bony resection will now be described more fully hereinafter with reference to the accompanying drawings, in which one or more features of the joint evaluation device will be shown and described. It should be appreciated that the various features may be used independently of, or in combination, with each other. It will be appreciated that a joint evaluation device as disclosed herein may be embodied in many different forms and should not be construed as being limited to the embodiments set forth herein. Rather, these embodiments are provided so that this disclosure will convey certain features of the joint evaluation device to those skilled in the art.

As will be described herein, in accordance with one or more features of the present disclosure, the joint evaluation device may be used to measure the joint laxity in a knee joint. In one embodiment, the joint evaluation device may be arranged and configured to be inserted into the knee joint prior to performing bony resection of the patient's tibia or femur. In addition, and/or alternatively, the joint evaluation device may be arranged and configured to be initially inserted into the knee joint without causing distraction or separation of the knee joint. In use, the joint evaluation device may be arranged and configured to measure a gap (e.g., distance) and/or a force between a patient's tibia and femur. However, it is envisioned that the joint evaluation device may be used in other joints such as, for example, a patient's shoulder. As such, the present disclosure should not be limited to a particular joint (e.g., a knee joint) unless specifically claimed.

As will be described herein, in accordance with one or more features of the present disclosure, the joint evaluation device includes first and second engagement portions such as, for example, first and second prongs, forks, or arms (terms such as engagement portions, prongs, forks, arms, etc. used interchangeably herein without the intent to limit). In use, the first and second engagement portions may be moved relative to each other. In use, in one embodiment, the first and second engagement elements can be inserted into the patient's joint such as, for example, into the patient's knee joint in-between the patient's tibia and femur, prior to bony resection. Thereafter, the first and second engagement portions may be moved relative to each other. During movement, the gap or distance between the patient's tibia and femur and/or the force exerted onto the first and second engagement portions by the patient's tibia and femur can be measured and monitored until a desired gap and/or desired force is achieved. For example, in one embodiment, the first and second engagement portions can be moved until a desired gap is achieved such as, for example, a rectangular gap is achieved indicating a consistent gap exists between the patient's tibial and femur in the medial/lateral direction. In addition, and/or alternatively, the first and second engagement portions can be moved until a desired force is achieved between the patient's tibial and femur indicating, for example, that the ligaments and knee are appropriately tensioned. Once achieved, the position of the patient's bone can be identified thereby assisting the surgeon with determining optimal implant positioning, which may then be used to plan resection and/or implant sizing.

Thus arranged, in accordance with one or more features of the present disclosure, the joint evaluation device enables the surgeon to determine joint laxity of the patient's joint prior to any bone resection. In addition, the joint evaluation device removes the necessity for the surgeon to introduce, for example, a surgical retractor, which induces a gap into the joint between the patient's bone, thus enabling the surgeon to reduce the minimum gap that can be measured as forces are induced to the joint. That is, in accordance with one or more features of the present disclosure, the joint evaluation device enables a surgeon to introduce one of the engagement portions into the patient's joint without increasing the native joint space between the patient's tibia and femur (e.g., the first engagement portion is arranged and configured to be inserted into the native space or gap existing between the patient's medial and lateral condyles and the patient's tibial (e.g., femoral notch)). Thereafter, the second engagement portion may be moved relative to the inserted first engagement portion in a lateral direction, all the while, the joint evaluation device enables the surgeon to measure the joint laxity (e.g., gap and/or force) being exerted onto the engagement portions and without the need for the patient's bone to be resected. As such, the joint evaluation device enables the surgeon to measure the joint laxity prior to distraction of the joint.

In use, as will be appreciated by one of ordinary skill in the art, the desired outcome may be predetermined or preselected by a surgeon based on, for example, past experience, preferences, a particular demographic, etc. For example, in one embodiment, a surgeon may desire to achieve a predetermined force between the patient's tibial and femur. Alternatively, and/or in addition, a surgeon may desire a predetermined distance or gap between the patient's tibial and femur. In accordance with one or more features of the present disclosure, the joint evaluation device may be used to constantly monitor the force and/or gap (e.g., distance) between the patient's tibial and femur. For example, using a CAS system, the force and/or gap may be displayed onto a viewing screen. As such, the surgeon can determine when the desired force and/or desired gap is achieved. At which point, the position of the patient's tibial and femur can be determined, which can be used to plan bony resection and/or implant sizing and positioning. Thus arranged, the gap between the patient's medial condyle and tibia and the lateral condyle and tibial can be consistent.

Referring to FIGS. 1-7, an embodiment of a joint evaluation device 100 arranged and configured to assess soft tissues in between bones of a patient's joint such as, for example, a knee joint 1000 in accordance with one or more features of the present disclosure will now be shown and described. As shown, the joint evaluation device 100 includes a body 101, a first engagement portion 110, and a second engagement portion 120.

As will be described in greater detail herein, the first and second engagement portions 110, 120 may be arranged and configured as prongs, forks, arms, etc. Alternatively, the engagement portions 110, 120 may be provided in other configurations. For example, it is envisioned that the first and second engagement portions may be provided in the form of nested components with at least one of the engagement portions being wedged shape. In use, the second engagement portion may be moved along or atop of the first engagement portion.

In use, the first and second engagement portions 110, 120 may be arranged and configured to move relative to each other. For example, with reference to FIGS. 1 and 2, the second engagement portion 120 is arranged and configured to move relative to the first engagement portion 110, although other configurations are envisioned. Thus arranged, in use, the joint evaluation device 100 may be generally provided in the form of a wrench-type device.

As illustrated, in one embodiment, the body 101 may include a handle 102 arranged and configured to be grasped by a user. In one embodiment, as illustrated, the handle 102 may be arranged and configured to extend substantially parallel with the direction of motion between the first and second engagement portions 110, 120 (as depicted by an arrow "X" in FIG. 2). Other embodiments may include other functional handles that enable grasping by a user or attachment to a surgical table, instrument, robotic arm, or other holding apparatus. By way of non-limiting example, with reference to FIG. 10, an alternate embodiment of a joint evaluation device 3100 may include a body 3101 including a handle 3102 oriented in a substantially perpendicular direction with the direction of motion between the first and second engagement portions 110, 120.

In addition, the joint evaluation device 100 also includes an actuator 130. In one embodiment, the actuator 130 is coupled to the body 101, 3101 of the joint evaluation device 100, 3100. In use, the actuator 130 is arranged and configured to move the first and second engagement portions 110, 120 relative to each other. In use, the actuator 130 may have any suitable arrangement and configuration suitable to move or drive the first and second engagement portions 110, 120 relative to each other. For example, in one embodiment, the actuator may be a manually actuated actuator such as, for example, a hand trigger such that moving first and second handle portions relative to each other moves the first and second engagement portions 110, 120 relative to each other. Alternatively, for example, as illustrated in FIGS. 1-7, the actuator 130 may be an electric motor, activation of which moves or drive the second engagement portion 120 relative to the first engagement portion 110. Alternatively, with reference to FIGS. 9 and 10, the actuator 2130 may be in the form of a thumbwheel, which may be arranged and configured to move or drive the first and second engagement portions 110, 120 relative to each other.

In either configuration, in one embodiment, the actuator 130, 2130 may be arranged and configured with a threaded shaft 140 and one or more gears 125. In use, in one embodiment, activation of the actuator 130 (e.g., electrical motor) is arranged and configured to rotate the threaded shaft 140 coupled to the body 101. The threaded shaft 140 being operatively coupled to the one or more gears 125, which are operatively coupled with the second engagement portion 120 so that activation of the actuator 130 rotates the threaded shaft 140, which rotates the gear(s) 125, which moves the second engagement portion 120 relative to the first engagement portion 110. Alternatively, in connection with the joint evaluation device 2100 illustrated in FIG. 9 and the joint evaluation device 3100 illustrated in FIG. 10, manually rotation of the actuator 2130 (e.g., thumbwheel) rotates the threaded shaft 140, which rotates the gear(s) 125, which moves the second engagement portion 120 relative to the first engagement portion 110. Embodiments of the joint evaluation device may include one or more batteries or electrical supply connections, as needed, to enable functions such as the electrical motor driven actuator, processor function, memory function, wireless connectivity, and force measuring sensors.

As will be described in greater detail herein, in use, the first engagement portion 110 may be arranged and configured to be inserted into a patient's joint such as, for example, a patient's knee joint in the native space created between the patient's tibia and the patient's medial and lateral condyles of the patient's femur (e.g., femoral notch). As such, the first engagement portion 110 may be inserted into the patient's joint space without affecting the gap or distance between the patient's tibial and femur. Thereafter, the second engagement portion 120 may be laterally moved relative to the first engagement portion 110 so that the second engagement portion 120 may be laterally inserted into the patient's joint.

In use, as the second engagement portion 120 is being laterally inserted and thus distracting the joint space between the patient's femur and tibia, the joint evaluation device 100, 2100, 3100 is arranged and configured to measure the force and/or gap (e.g., distance) in the patient's joint. For example, in one embodiment, the joint evaluation device 100, 2100, 3100 may be arranged and configured to measure the force on the actuator 130, 2130 required to move the second engagement portion 120 through the patient's joint space. The force on the actuator 130, 2130 being correlated as a measurement of the implied force or tension on the joint. Alternatively, referring to FIGS. 8A and 8B, and as will be described in greater detail herein, an alternate embodiment of a joint evaluation device 1100 includes first and second engagement portions 1110, 1120 including an array of force or pressure sensors 1117, 1127 thereon arranged and configured to measure the force on the first and second engagement portions 1110, 1120 of the joint evaluation device 1100. Thereafter, in use, when the desired force and/or desired gap is determined by the surgeon such that the gap and/or force between, for example, the lateral condyle and the tibia and the medial condyle and tibia are equal, the position of the patient's bones can be recorded, the bony resections can be performed, and the knee implant implanted in order to achieve the desired balanced knee.

With continued reference to the FIGS., and as previously mentioned, the first engagement portion 110 may be fixedly coupled to the body 101, 3101. The second engagement portion 120 may be moveably or slidably coupled to the body 101, 3101 so that the second engagement portion 120 may be moved relative to the first engagement portion 110. In other embodiments, the first engagement portion 110 may be moveably or slidably coupled to the body 101, 3101 while the second engagement portion 120 may be fixedly coupled to the body 101, 3101 so that the first engagement portion 110 may be moved relative to the second engagement portion 120. Moreover, in other embodiments, the first and second engagement portions 110, 120 may each be moveably or slidably coupled to the body 101, 3101 so that the first and second engagement portions 110, 120 are moveable relative to each other.

In use, in one embodiment, the second engagement portion 120 may be moveable via activation of the actuator 130, 2130 or other components to facilitate movement of the second engagement portion 120 relative to the body 101, 3101 and/or the first engagement portion 110. In use, the force exerted by the actuator 130, 2130 to move the second engagement portion 120 through the joint space may be measured, determined, etc. For example, as previously described, the second engagement portion 120 may be moved by activation of the electrical motor or by turning the thumbwheel. The measured force on the actuator 130, 2130 may then be correlated as a measurement of the implied force or tension on the joint. Thereafter, in use, when the desired force is determined by the surgeon such that the force between the lateral condyle and the tibia and the medial condyle and tibia are equal, the position of the patient's bones can be recorded, the bony resections can be performed, and the implant implanted in order to achieve the desired balanced knee.

In one embodiment, as shown in FIGS. 1, 2, 4, 5, 7, 8A, 8B, and 10, the first engagement portion 110, 1110 includes a first face 116, 1116. The second engagement portion 120, 1120 includes a second face 126, 1126. As illustrated, in one embodiment, the first face 116, 1116 is arranged and configured at an oblique angle relative to the direction of motion (arrow "X" in FIG. 2) between the first and second engagement portions 110, 1110, 120, 1120. Similarly, the second face 126, 1126 is arranged and configured at an oblique angle relative to the direction of motion (arrow "X" in FIG. 2) between the first and second engagement portions 110, 1110, 120, 1120.

In addition, in accordance with one or more features of the present disclosure, the joint evaluation device 100, 1100, 2100, 3100 may include or be operatively associated with one or more force measurement devices arranged and configured to evaluate, measure, determine, calculate, etc. (terms used interchangeably herein without the intent to limit) a force applied between the first engagement portion 110, 1110 and the second engagement portion 120, 1120. For example, in one embodiment, the force measurement device may be incorporated into the joint evaluation device 100, 1100, 2100, 3100. Alternatively, the force measurement device may be incorporated into a system including the joint evaluation device 100, 1100, 2100, 3100.

That is, in accordance with one or more features of the present disclosure, the joint evaluation device 100, 1100, 2100, 3100 is arranged and configured to evaluate how much force is being exerted on the soft tissues of a patient's joint such as, for example, the patient's knee. However, in use, since the first engagement portion 110, 1110 and the second engagement portion 120, 1120 are being moved substantially perpendicular to the direction of the forces being exerted on the soft tissues of the knee (e.g., the second engagement portion 120, 1120 is being moved laterally through the patient's joint relative to the first engagement portion 110, 1110), the force being exerted on the soft tissues of the patient's knee is not measured directly. As such, by incorporating inclined first and second faces 116, 1116, 126, 1126 on the first and second engagement portions 110, 1110, 120, 1120, respectively, the inclined first and second faces 116, 1116, 126, 1126 serve to redirect the forces generated by movement of the second engagement portion 120, 1120 relative to the first engagement portion 110, 1110 in a direction of relative longitudinal movement of the patient's tibia and femur to thereby exert a force on the soft tissues of the patient's knee.

Thus, in accordance with one or more features of the present disclosure, the force required to move the first and second engagement portions 110, 1110, 120, 1120 relative to each other is proportional to the force being exerted on the soft tissues of the patient's knee. As such, by evaluating the force required to move the first and second engagement portions 110, 1110, 120, 1120 relative to each other, the force being exerted on the soft tissues of the patient's knee can be evaluated. Thereafter, in use, by evaluating the force being exerted on the soft tissues of the patient's knee, the surgeon can better optimize the position of the patient's femur relative to the patient's tibial to create a balanced knee.

In accordance with one or more features of the present disclosure, the force measurement device may be any suitable device or mechanism now known or hereafter developed to evaluate the force required to move the first and second engagement portions 110, 1110, 120, 1120 relative to each other laterally through the joint space. For example, in one embodiment, the force measurement device may be associated with the actuator 130 such as, for example, the electrical motor. In use, the force measurement device may be arranged and configured to measure the torque required to turn the electrical motor. The torque or force measurement may be associated with the amount of electrical energy required to turn the motor or may be from a stress measurement, strain measurement, or any other kind of effective measurement device or technique that is proportional to the force being exerted on the soft tissues of the knee joint and, which is readily calculable. Force measurement may also be associated with compression or tension created in components as a result of turning the actuator 130 and not necessarily be associated with a torque measurement.

Figure 9:
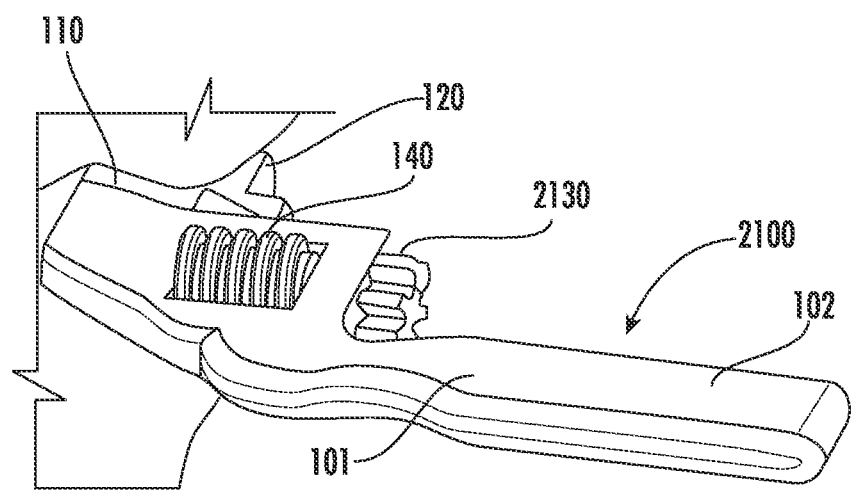
FIG. 9 is a perspective view of another embodiment of a joint evaluation device for assessing soft tissues of a knee joint in accordance with one or more features of the present disclosure, the joint evaluation device including a manually engageable thumbwheel adjustment mechanism.
Figure 10:
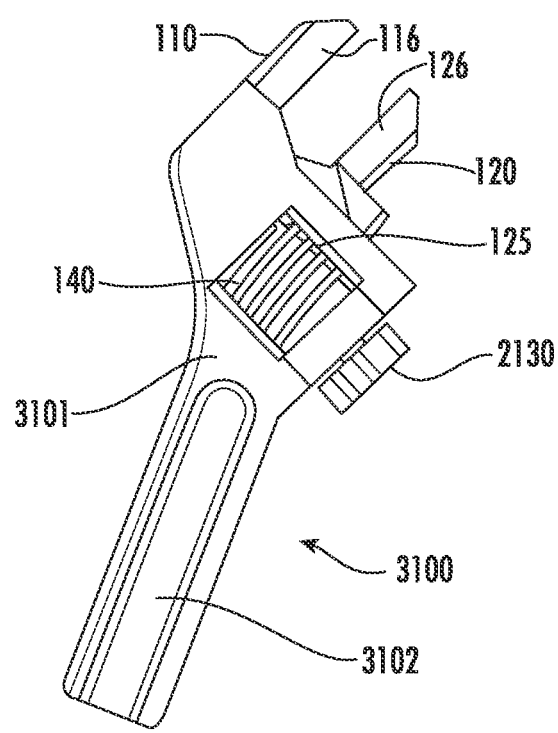
FIG. 10 is a perspective view of another embodiment of a joint evaluation device for assessing soft tissues of a knee joint in accordance with one or more features of the present disclosure, the joint evaluation device including an alternatively oriented handle.

Alternatively, with reference to FIGS. 9 and 10, the force measurement device may be associated with the actuator 2130 such as, for example, the manually actuated thumbwheel. In use, in one embodiment, the force measurement device may be positioned between the thumbwheel and the body 2101, 3101 to measure the force required to turn the thumbwheel. As previously described, in use, rotation of the actuator 2130 (e.g., thumbwheel) results in turning of the threaded shaft 140 to engage with gears 125 (FIG. 10) on the second engagement portion 120 to move the second engagement portion 120 relative to the first engagement portion 110. The torque or force measurement may be from a stress measurement, strain measurement, or any other kind of effective measurement device or technique that is proportional to the force being exerted on the soft tissues of the patient's knee and, which is readily calculable. Force measurement may also be associated with compression or tension created in components as a result of turning the actuator 2130.

Figure 8A:
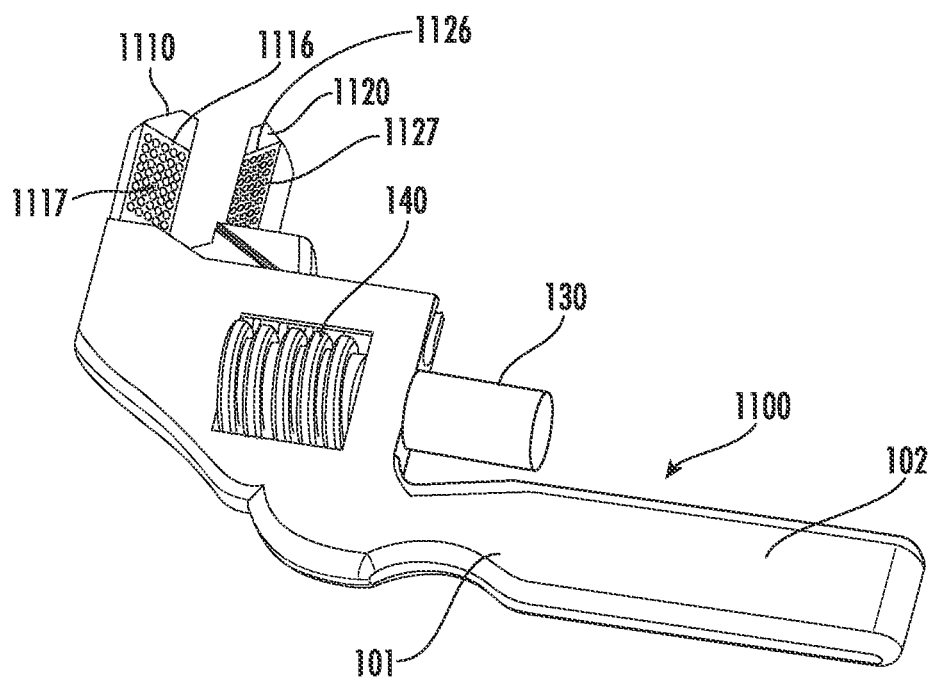
FIG. 8A is a perspective view of another embodiment of a joint evaluation device for assessing soft tissues of a knee joint in accordance with one or more features of the present disclosure, the joint evaluation device including force or pressure sensors on inclined faces of the device.
Figure 8B:
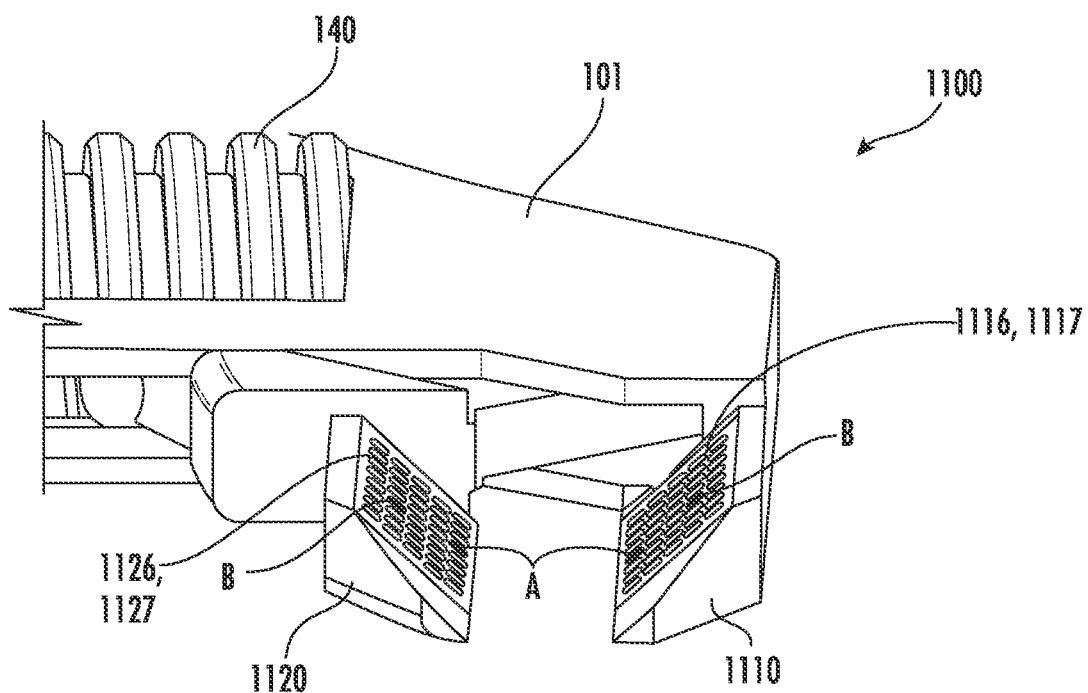
FIG. 8B is a detailed, perspective view of the joint evaluation device of FIG. 8A.

Alternatively, with reference to FIGS. 8A and 8B, in one embodiment, the first face such as, for example, the first face 1116 of the first engagement portion 1110 and the second face such as, for example, the second face 1126 of the second engagement portion 1120 may each include an array of sensors 1117, 1127 thereon. That is, in one embodiment, the force measurement device may be in the form of an array of force or pressure sensors 1117 positioned on the first face 1116 of the first engagement portion 1110 and an array of force or pressure sensors 1127 positioned on the second face 1126 of the second engagement portion 1120, although it is envisioned that only one of the first and second faces 1116, 1126 may include an array of sensors thereon. In use, the array of sensors 1117, 1127 are arranged and configured to measure the force or pressure on the first and second faces 1116, 1126 of the first and second engagement portions 1110, 1120. That is, the array of sensors 1117, 1127 are arranged and configured to measure the force or pressure applied onto the first and second faces 1116, 1126, which force is proportional to the force or pressure being exerted on the soft tissues of the patient's knee, and may therefore also be used to evaluate the force or pressure being exerted on the soft tissues of the patient's knee. As such, rather than measuring the force applied by the actuator (e.g., motor, thumbwheel, etc.) to move the first and second engagement portions 110, 120 relative to each other through the joint, the array of sensors 1117, 1127 can measure the force or pressure being applied by the joint onto the first and second engagement portions 1110, 1120.

In use, the force or pressure sensors 1117, 1127 may be any suitable force or pressure sensors now known or hereafter developed. For example, in one embodiment, the sensors 1117, 1127 may be an electronically controlled thin film sensor. In one embodiment, the array of force sensors 1117, 1127 may be arranged and configured as a disposable strip so that the array of force sensors 1117, 1127 may be coupled to the first and second faces 1116, 1126 of the first and second engagement portions 1110, 1120. Thus arranged, the array of force sensors 1117, 1127 may be exchanged, for example, after each use. Alternatively, the array of force sensors 1117, 1127 may be reusable and/or permanently attached to the first and second faces 1116, 1126 of the first and second engagement portions 1110, 1120.

In use, by incorporating an array of sensors 1117, 1127 onto the first and second faces 1116, 1126 of the first and second engagement portions 1110, 1120, the joint evaluation device 1100 can be arranged and configured to calculate the displacement of the joint from the relative movement of the tracking probes (as will be described in greater detail below) and change in contact point on the array of sensors 1117, 1127. That is, in use, the array of sensors 1117, 1127 are arranged and configured to detect loading on the first and second faces 1116, 1126 of the first and second engagement portions 1110, 1120. For example, in one method of use, the joint evaluation device 1100 can be inserted into the patient's joint as described herein. With the joint evaluation device 1100 positioned in a home position, as generally illustrated in FIG. 8B, the initial point of contact between the array of sensors 1117, 1127 on the first and second faces 1116, 1126 of the first and second engagement portions 1110, 1120 can be determined. Thereafter, the first and second engagement portions 1110, 1120 can be moved relative to each other until the desired gap and/or desired force in the joint is achieved. Once determined, the final point of contact between the array of sensors 1117, 1127 on the first and second faces 1116, 1126 of the first and second engagement portions 1110, 1120 can be determined.

For example, with reference to FIG. 8B, the joint evaluation device 1100 is arranged and configured to determine the relative displacement in the patient's joint based on relative movement of the engagement portions 1110, 1120. In one embodiment, the initial position of the first and second engagement portions 1110, 1120 may be established. As such, the initial or home position of the first and second engagement portions 1110, 1120 relative to each other may be established (e.g., the relative distance between the first and second engagement portions 1110, 1120 relative to each other may be determined). Thereafter, the joint evaluation device 1100 may be inserted into the patient's joint and the initial point of contact between the array of sensors 1117, 1127 on the first and second engagement portions 1110, 1120 and the patient's femur can be determined. For example, the initial point of contact between the patient's bone (e.g., femur) and the array of sensors 1117, 1127 on the first and second engagement portions 1110, 1120 may correspond to point A in FIG. 8B. Next, the patient's joint may be tensioned by, for example, reducing or decreasing the distance between the first and second engagement portions 1110, 1120 of the joint evaluation device 1100 (e.g., the first and second joint engagement portions 1110, 1120 may be brought closer together). The patient's joint may be tensioned until a predetermined target force (e.g., load) and/or distance is achieved, which may correspond, for example, with a different sensor 1117, 1127 on the first and second engagement portions 1110, 1120. For example, the final or desired point of contact between the patient's bone (e.g., femur) and the array of sensors 1117, 1127 on the first and second engagement portions 1110, 1120 may correspond to point B in FIG. 8B. In use, by calculating the displacement or difference in contact points between the array of sensors 1117, 1127 and the patient's femur, we can calculate the displacement of the patient's joint (e.g., measure the joint gap). As such, reliance on trackers and cameras is no longer necessary.

Figure 11:
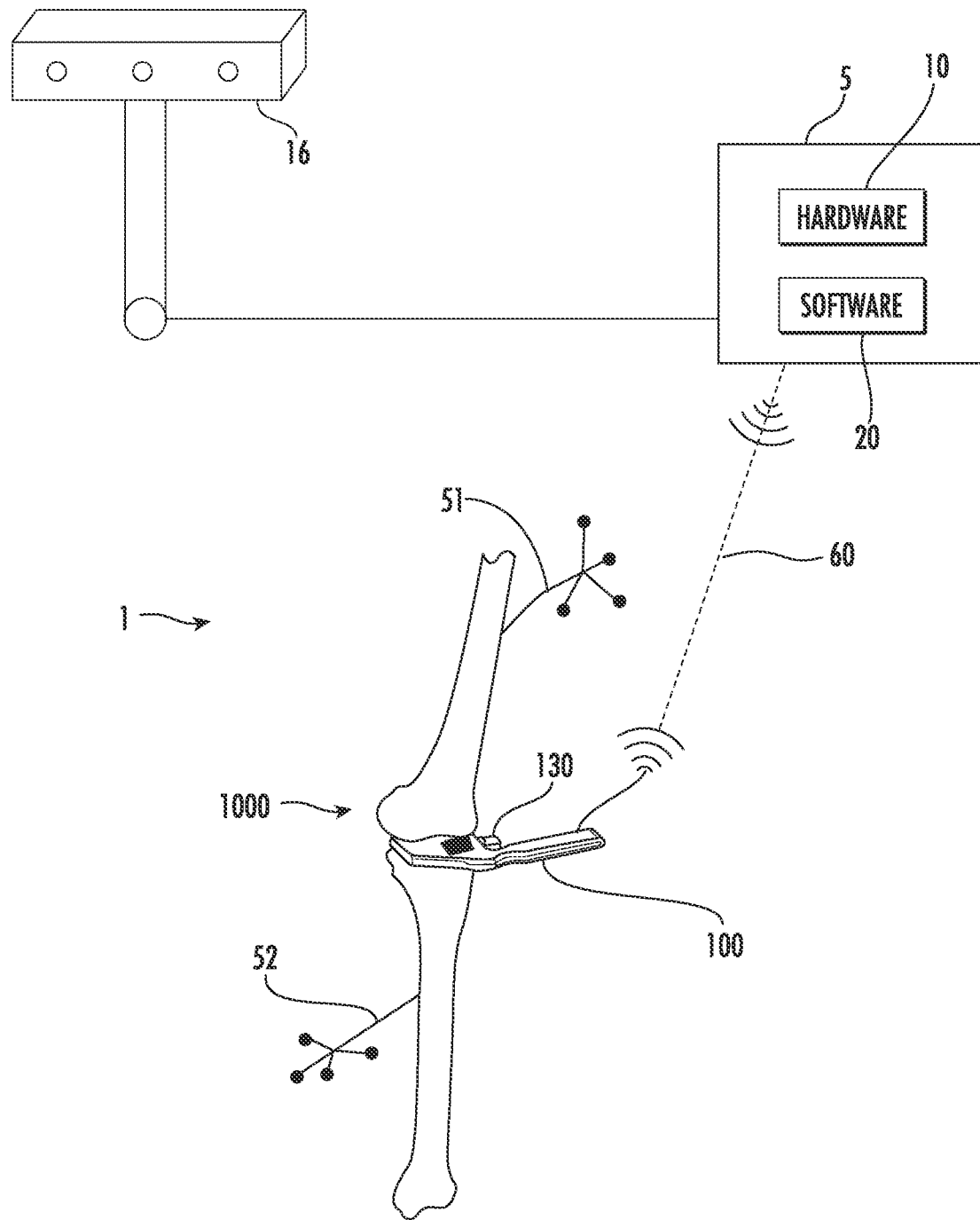
FIG. 11 is a system diagram of a joint evaluation device for assessing soft tissues of a knee joint in accordance with one or more features of the present disclosure, the joint evaluation device positioned within a patient's knee joint and also schematically illustrating a CAS system components and computing device hardware and software.

Referring to FIG. 11, an embodiment of a computer assisted surgery (CAS) device or system 1 (terms used interchangeably herein without the intent to limit) arranged and configured to evaluate ligament and other soft tissue connections between, for example, a tibia and a femur at a knee joint 1000 is illustrated. As illustrated, a joint evaluation device 100, as previously described herein, is shown inserted into the patient's knee joint 1000 in-between the patient's femur and the patient's tibia. In other embodiments, the joint evaluation devices 1100, 2100, 3100, or other similar devices, may be used in place of the joint evaluation device 100.

In use, in one embodiment, the CAS system 1 is arranged and configured to track the relative locations of the patient's tibia and femur of the knee joint 1000. For example, as illustrated, the CAS system 1 may include tracking arrays 51, 52, a position sensor 16, and a computing device 5. As will be readily appreciated by one of ordinary skill in the art, the tracking arrays 51, 52 may include tracked elements or fiducials trackable by one or more of electromagnetic, electrostatic, light sound, radiofrequency or other energy sources. In use, the tracking arrays 51, 52 may be coupled to the patient's bone by any suitable mechanism now known or hereafter developed including, for example, screw driven into the bone, or any other three dimensional item attached to another item, the position and orientation of such three dimensional item able to be tracked in order to track position and orientation of the patient's body parts (e.g., bones) and surgically related items. Fiducials may be partly passive or partly active, such as inductive components or transponders which respond with a certain signal or data set when queried by sensors according to the present disclosure.

The computing device 5 may include associated hardware 10 and software 20. In use, the computing device 5 is arranged and configured to communicate with the joint evaluation device 100 of the system 1. In addition, the computing device 5 is arranged and configured to evaluate the forces being exerted on the soft tissues of the knee. Alternatively, the evaluating may be shared by each component in whole or in part in various embodiments.

In use, the computing device 5 may calculate and store position data regarding the tibia and femur to which the tracking arrays 51, 52 are coupled. In use, the CAS system 1 provides information about balancing of the ligaments and soft tissues and can suggest or at least provide more accurate information about implant sizing, resection locations, and which ligaments the surgeon should release in order to obtain correct balancing, alignment, and stability. Systems according to the present disclosure can also suggest modifications to implant size, positioning, and other techniques to achieve optimal kinematics. Systems according to the present disclosure can also include databases of information regarding tasks such as ligament balancing, in order to provide suggestions to the surgeon based on performance of test results as automatically calculated by such systems and processes.

The position sensor 16, as mentioned above, may be any sort of sensor functionality for sensing position and orientation of fiducials, and therefore items with which they are associated, according to whatever desired electrical, magnetic, electromagnetic, sound, physical, radio frequency, or other active or passive technique is used. In the illustrated embodiment, the position sensor 16 is a pair of infrared sensors disposed apart and whose output can be processed in concert to provide position and orientation information regarding fiducials.

In the embodiment shown, the computing device 5 may include processing functionality, memory functionality, input/output functionality, whether on a standalone or distributed basis, through any desired standard, architecture, interface and/or network topology. The computing device 5 may be connected to a monitor on which graphics and data may be presented to the surgeon during surgery. The screen may have a tactile interface, a keyboard, and a mouse, or other interfaces. Additionally, a foot pedal or other convenient interface may be included, as can any other wireless or wireline interface to allow the surgeon, nurse, or other desired user to control or direct functionality.

In the illustrated embodiment, the computing device 5 may be arranged and configured to evaluate the forces measured between the first engagement portion 110, 1110 and the second engagement portion 120, 1120 and to output information related to the status of the ligament and other soft tissue connections between the tibia and the femur of the knee joint 1000 prior to any bone resections being made to the tibia or the femur. The phrase "prior to any bone resections," is referring to significant resections, and not preparatory cuts or removals such as tissue clearing for instrument access, node removals, bone abnormality removals, etc.

As shown in FIG. 11, force measurement information may be transmitted between the joint evaluation device 100 and the computing device 5 over a wireless connection 60. Other embodiments may include other wireless or wireline connections. In some embodiments, output information related to the status of the ligament and other soft tissue connections between the tibia and the femur of the knee calculated by the computing device 5 includes implant size and location recommendations that may be used by a surgeon to select effective implants and plan for placement of the implants. Output information related to the status of the ligament and other soft tissue connections between the tibia and the femur of the knee calculated by the computing device 5 may include one or both of tibia and femur resection cut locations recommendations that may be used by a surgeon to make surgical cuts.

Figure 3:
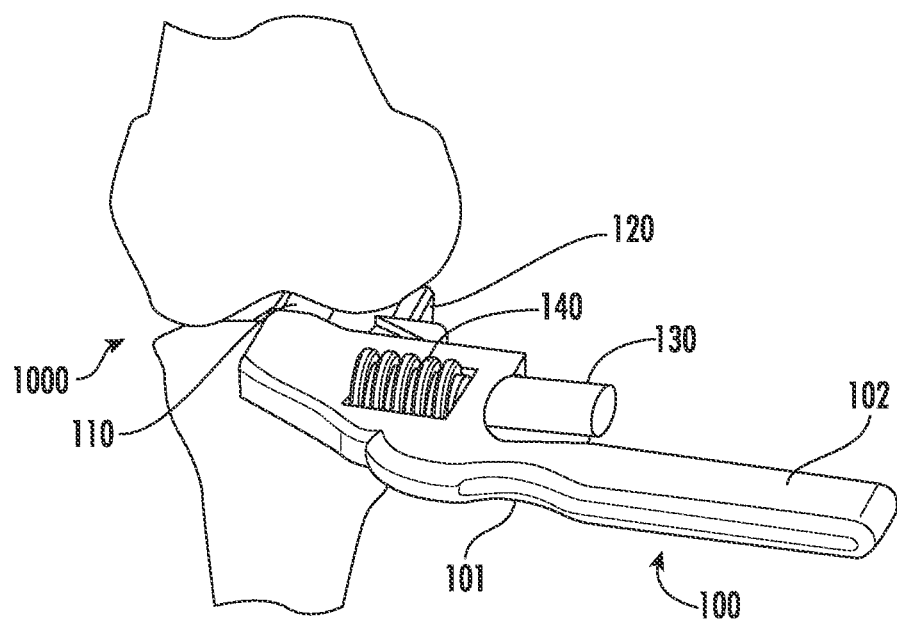
FIG. 3 is a generally anterior perspective view of the joint evaluation device of FIG. 1, the joint evaluation device shown illustrated post-insertion into a lateral side of the knee joint in an open state.
Figures 4, 5:
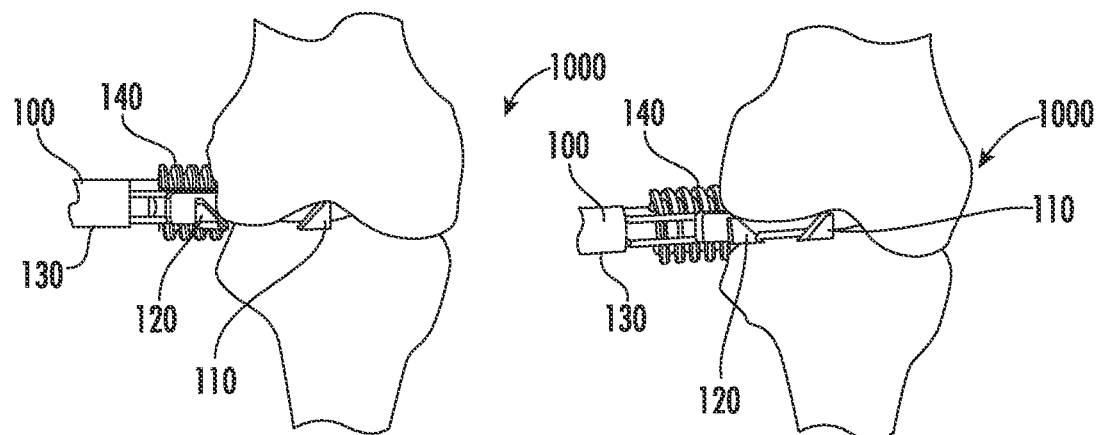
FIG. 4 is a posterior elevation view of the knee joint and joint evaluation device as shown in FIG. 3.
FIG. 5 is a posterior elevation view of the knee joint and the joint evaluation device as shown in FIG. 3, the joint evaluation device illustrated in a relatively more closed state at the lateral side of the knee joint.
Figure 6:
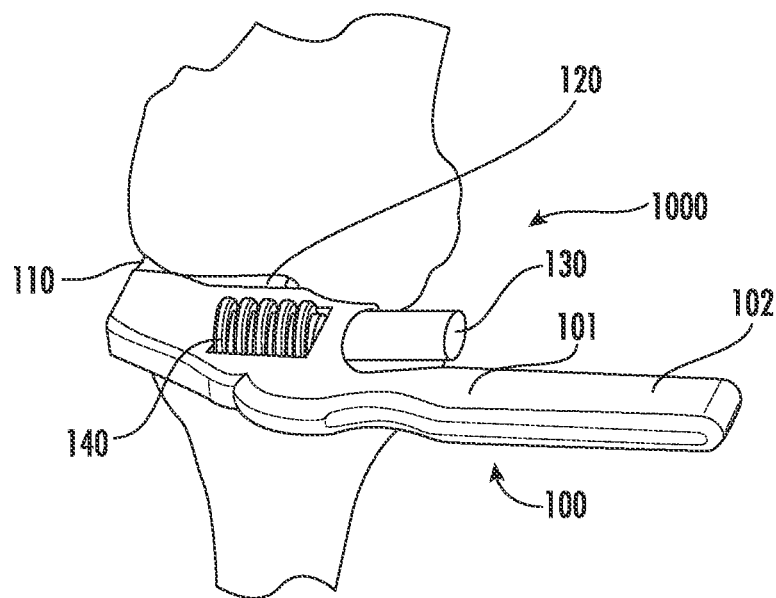
FIG. 6 is a generally anterior perspective view of the joint evaluation device of FIG. 1, the joint evaluation device illustrated post-insertion into a medial side of the knee joint in an open state.
Figure 7:
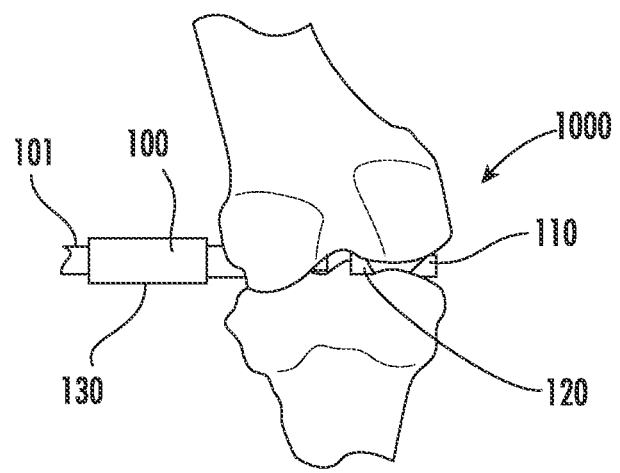
FIG. 7 is a posterior elevation view of the knee joint and the joint evaluation device of FIG. 1, the joint evaluation device illustrated in a relatively more closed state at the medial side of the knee joint.

An embodiment of a method of evaluating the soft tissues of a patient's joint such as, for example, a patient's knee is disclosed. In use, the method can be accomplished with the devices and systems disclosed in FIGS. 1-11, as is further describe herein. In one embodiment, the method may include inserting a first engagement portion 110, 1110 and a second engagement portion 120, 1120 of a joint evaluation device 100, 1100, 2100, 3100 into a knee joint 1000 between a femur and a tibia, as specifically shown in FIGS. 3-7, 9, and 11. The act of inserting, for example, the first engagement portion 110 and the second engagement portion 120 of the joint evaluation device 100 into the knee joint 1000 between a femur and a tibia, as illustrated in FIGS. 3-5, depicts inserting one engagement portion into the femoral notch and the other engagement portion on a lateral side of the patient's knee 1000. In one embodiment, the first engagement portion 110 may be inserted into the femoral notch and the second engagement portion 120 may be positioned on the lateral side of the knee 1000. The act of inserting the first engagement portion 110 and the second engagement portion 120 of the joint evaluation device 100 into the knee joint 1000 between a femur and a tibia, as illustrated in FIGS. 6 and 7, depicts inserting one engagement portion into the femoral notch and the other engagement portion on a medial side of the patient's knee 1000. In one embodiment, the first engagement portion 110 may be positioned on the medial side of the knee 1000 and the second engagement portion 120 may be inserted into the femoral notch. In other embodiments, one engagement portion may be inserted on a medial side of the knee 1000 while the other engagement portion is inserted on a lateral side of the knee 1000. In one embodiment, the surgeon may initially insert one engagement portion into the femoral notch and the other engagement portion on a lateral side of the patient's knee 1000. Thereafter, once the appropriate evaluating of the patient's knee has been completed, the surgeon may insert one engagement portion into the femoral notch and the other engagement portion on a medial side of the patient's knee 1000, or vice-versa.

The method may also include moving the first engagement portion 110, 1110 and the second engagement portion 120, 1120 of the joint evaluation device 100, 1100, 2100, 3100 relative to each other to create a relative movement of the patient's femur and tibia. For example, referring to FIGS. 1, 2, and 4-7, relative movement of the femur and the tibia is accomplished by wedging apart the femur and the tibia with both the first engagement portion 110, 1110 and the second engagement portion 120, 1120 by moving the first and second engagement portions 110, 1110, 120, 1120 towards each other. In other embodiments, it is contemplated that either a first engagement portion or a second engagement portion, but not both, includes a wedging element. In other embodiments, wedging apart the femur and the tibia may be accomplished be moving a first engagement portion and a second engagement portion away from each other.

The method may also include measuring the force required to move the first engagement portion 110, 1110 and the second engagement portion 120, 1120 of the joint evaluation device 100, 1100, 2100, 3100 relative to each other to create a relative movement of the femur and the tibia. As previously described herein, the act of measuring may be accomplished using a force sensor located on a surface of an engagement member, such as the array of force or pressure sensors 1117, 1127 to measure components of the force applied between the first face 1116 and the second face 1126 that are proportional to the force being exerted on the soft tissues of the patient's knee, and may therefore also be used to evaluate the force being exerted on the ligaments and other soft tissues of the patient's knee 1000. Alternatively, as previously described herein, measuring the force required to move the first engagement portion 110 and the second engagement portion 120 of the joint evaluation device 100, 2100, 3100 relative to each other to create a relative movement of the femur and the tibia in some embodiments includes measuring a force required to turn the actuator 130, 2130 (e.g., motor, thumbwheel, etc.) that is positioned between the first engagement portion 110 and the second engagement portion 120. In one embodiment, the torque or force measurement may correlate with the amount of electrical energy required to turn the motor or may be derived from a stress measurement, strain measurement, or any other kind of effective measurement device or technique that is proportional to the force being exerted on the soft tissues of the knee. Force measurement may also be associated with compression or tension created in components as a result of turning the actuator 130, 2130 and not necessarily associated with a torque measurement.

In some embodiments, the relative movement of the femur and the tibia is measured using a CAS system 1, as previously illustrated and described in connection with FIG. 11. Measurement of the forces collected by the joint evaluation device 100, 1100, 2100, 3100 may be transmitted to the computing device 5 where hardware 10 and software 20 execute instructions that allow certain levels of measured force to cause the CAS system 1 to measure and record the relative movement and positions of the tibia and the femur. Similarly, recording of the relative movement of the femur and the tibia may be accomplished periodically through a range of motion, while at the same time force measurements are being captured by the joint evaluation device 100, 1100, 2100, 3100. This functionality allows the user to quantify a stress-strain relationship, and resulting curve, for the knee ligaments and other soft tissues over range of loadings. Such a measurement method provides a repeatable measurement technique for quantifying ligament and soft tissue properties.

Consequently, the methods are able to employ the computing device 5 to calculate information related to the status of the ligament and other soft tissue connections between the tibia and the femur based on the force required to move the first engagement portion 110, 1110 and the second engagement portion 120, 1120 of the joint evaluation device 100, 1100, 2100, 3100 relative to each other and the measured relative movement of the femur and the tibia. Under the technique disclosed, this information may be calculated prior to any bone resections being made to the tibia or the femur, which is a significant improvement to present systems and methods in the field.

Method embodiments may also include using the calculated information to output surgical instructions. For example and without limitation, the surgical instructions may include specification of implant size or sizes and placement location recommendations. Some embodiments may also output surgical instructions specifying resection cut position recommendations for some or all of the implants to be place.

Various embodiments of the system in whole or its components individually may be made from any biocompatible material. For example, and without limitation, biocompatible materials may include in whole or in part: non-reinforced polymers, reinforced polymers, metals, ceramics, adhesives, reinforced adhesives, and combinations of these materials. Reinforcing of polymers may be accomplished with carbon, metal, or glass or any other effective material. Examples of biocompatible polymer materials include polyamide base resins, polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol and other superelastic or shape-memory metal alloys.

The foregoing description has broad application. While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments. Rather these embodiments should be considered as illustrative and not restrictive in character. All changes and modifications that come within the spirit of the disclosure are to be considered within the scope of the disclosure. The present disclosure should be given the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art. Unless otherwise defined, all technical terms used herein have the same meaning as commonly understood by one of ordinary skill in the art to which the disclosure belongs.

Directional terms such as top, bottom, superior, inferior, medial, lateral, anterior, posterior, proximal, distal, upper, lower, upward, downward, left, right, longitudinal, front, back, above, below, vertical, horizontal, radial, axial, clockwise, and counter-clockwise) and the like may have been used herein. Such directional references are only used for identification purposes to aid the reader's understanding of the present disclosure. For example, the term "distal" may refer to the end farthest away from the medical professional/operator when introducing a device into a patient, while the term "proximal" may refer to the end closest to the medical professional when introducing a device into a patient. Such directional references do not necessarily create limitations, particularly as to the position, orientation, or use of this disclosure. As such, directional references should not be limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However, such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. Furthermore, references to "one embodiment" of the present disclosure are not intended to be interpreted as excluding the existence of additional embodiments that also incorporate the recited features.

In addition, it will be appreciated that while the Figures may show one or more embodiments of concepts or features together in a single embodiment of an environment, article, or component incorporating such concepts or features, such concepts or features are to be understood (unless otherwise specified) as independent of and separate from each other and are shown together for the sake of convenience and without intent to limit to being present or used together. For instance, features illustrated or described as part of one embodiment can be used separately, or with another embodiment to yield a still further embodiment. Thus, it is intended that the present subject matter covers such modifications and variations as come within the scope of the appended claims and their equivalents.

As used herein, an element or step recited in the singular and proceeded with the word "a" or "an" should be understood as not excluding plural elements or steps, unless such exclusion is explicitly recited. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

The phrases "at least one", "one or more", and "and/or", as used herein, are open-ended expressions that are both conjunctive and disjunctive in operation. The terms "a" (or "an"), "one or more" and "at least one" can be used interchangeably herein.

Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The drawings are for purposes of illustration only and the dimensions, positions, order and relative to sizes reflected in the drawings attached hereto may vary.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments or configurations. Moreover, the following claims are hereby incorporated into this Detailed Description by this reference, with each claim standing on its own as a separate embodiment of the present disclosure.

We claim:

1. A method of evaluating a ligament and other soft tissues connections between a patient's tibia and a patient's femur of a knee joint, comprising:
    positioning a joint evaluation device adjacent to the patient's knee including inserting a first engagement portion of the joint evaluation device into a femoral notch between the medial and lateral condyles of the knee joint between the patient's tibia and femur, and positioning a second engagement portion of the joint evaluation device on one of a medial side or a lateral side of the knee joint, wherein the first engagement portion is inserted into the knee joint without affecting a distance between the patient's tibia and femur;
    moving the first and second engagement portions relative to each other such that the second engagement portion moves along a body of the joint evaluation device towards the first engagement portion to create a relative movement of the patient's tibia and femur;
    measuring a distance between the patient's tibia and femur as the first and second engagement portions are moved relative to each other;
    calculating information related to a status of the ligament and other soft tissues connections between the patient's tibia and femur based on the distance between the patient's tibia and femur prior to any bone resections being made to the patient's tibia and femur; and
    using the calculated information to output surgical instructions.

2. The method of claim 1, wherein the first engagement portion is inserted into the knee joint in a native space created between the patient's tibia and the patient's medial and lateral condyles of the patient's femur.

3. The method of claim 1, wherein moving the first and second engagement portions relative to each other such that the second engagement portion moves toward the first engagement portion to create a relative movement of the patient's tibia and femur includes wedging apart the patient's tibia and femur with one or both of the first and second engagement portions.

4. The method of claim 1, wherein the output surgical instructions include instructions specifying one of implant size and location recommendations, resection cut position recommendations, or a combination thereof.

5. The method of claim 1, wherein a sensor is used to determine a position of the first engagement portion and/or the second engagement portion.

6. The method of claim 5, wherein the sensor determines an orientation of the first engagement portion and/or the second engagement portion.

7. The method of claim 1, wherein the first and second engagement portions are moved relative to each other using an actuator.

8. The method of claim 7, wherein the actuator includes a motor.

9. The method of claim 8, wherein the motor is arranged and configured to turn a threaded shaft coupled to the body, the threaded shaft operatively coupled with one or more gears on the second engagement portion to move the second engagement portion relative to the first engagement portion when the motor is activated.

10. The method of claim 7, wherein the actuator includes a thumbwheel.

11. The method of claim 10, wherein the thumbwheel is arranged and configured to turn a threaded shaft, the threaded shaft operatively coupled with one or more gears on the second engagement portion to move the second engagement portion relative to the first engagement portion when the thumbwheel is actuated.

12. The method of claim 1, wherein the joint evaluation device further includes:
    the body;
    the first engagement portion coupled to the body;
    the second engagement portion coupled to the body;
    an actuator coupled to the body and configured to move the first and second engagement portions relative to each other; and
    a measurement device arranged and configured to evaluate a distance between the patient's tibia and femur as the second engagement portion is laterally moved towards the first engagement portion through the knee joint.

13. The method of claim 12, wherein the joint evaluation device further includes a sensor to determine a position and orientation of the first engagement portion and/or the second engagement portion.

14. The method of claim 1, wherein:
    the first engagement portion includes a first face arranged and configured at an oblique angle to a direction of motion between the first and second engagement portions; and
    the second engagement portion includes a second face arranged and configured at an oblique angle to the direction of motion between the first and second engagement portions.

* * * * *